US006670355B2

(12) United States Patent
Azrolan et al.

(10) Patent No.: US 6,670,355 B2
(45) Date of Patent: Dec. 30, 2003

(54) METHOD OF TREATING CARDIOVASCULAR DISEASE

(75) Inventors: Neal I. Azrolan, Lawrenceville, NJ (US); Steven J. Adelman, Doylestown, PA (US); Surendra N. Sehgal, deceased, late of Snohomish, WA (US), by Uma Sehgal, legal representative

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/313,217

(22) Filed: Dec. 6, 2002

(65) Prior Publication Data

US 2003/0149070 A1 Aug. 7, 2003

Related U.S. Application Data

(63) Continuation-in-part of application No. 09/880,295, filed on Jun. 13, 2001, now abandoned.
(60) Provisional application No. 60/212,117, filed on Jun. 16, 2000.

(51) Int. Cl.[7] .................... A61K 31/33; A61K 31/44; A61K 31/34
(52) U.S. Cl. .................... 514/183; 514/291; 514/470
(58) Field of Search ................ 514/183, 291, 514/470

(56) References Cited

U.S. PATENT DOCUMENTS

| | | |
|---|---|---|
| 3,929,992 A | 12/1975 | Sehgal et al. |
| 3,993,749 A | 11/1976 | Sehgal et al. |
| 4,316,885 A | 2/1982 | Rakhit |
| 4,401,653 A | 8/1983 | Eng |
| 4,650,803 A | 3/1987 | Stella et al. |
| 4,885,171 A | 12/1989 | Surendra et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Calne |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,206,018 A | 4/1993 | Sehgal et al. |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,262,423 A | 11/1993 | Kao |
| 5,286,730 A | 2/1994 | Caufield et al. |
| 5,286,731 A | 2/1994 | Caufield et al. |
| 5,288,711 A | 2/1994 | Mitchell et al. |
| 5,302,584 A | 4/1994 | Kao et al. |
| 5,321,009 A | 6/1994 | Baeder et al. |
| 5,362,718 A | 11/1994 | Skotnicki et al. |
| 5,373,014 A | 12/1994 | Failli et al. |
| 5,385,908 A | 1/1995 | Nelson et al. |
| 5,385,909 A | 1/1995 | Nelson et al. |
| 5,385,910 A | 1/1995 | Ocain et al. |
| 5,387,589 A | 2/1995 | Kulkarni |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,496,832 A | 3/1996 | Armstrong |
| 5,504,091 A | 4/1996 | Molnar-Kimber et al. |
| 5,516,770 A | 5/1996 | Waranis et al. |
| 5,516,781 A | 5/1996 | Morris et al. |
| 5,530,006 A | 6/1996 | Waranis et al. |
| 5,536,729 A | 7/1996 | Waranis et al. |
| 5,559,121 A | 9/1996 | Harrison et al. |
| 5,561,138 A | 10/1996 | Armstrong |
| 5,616,588 A | 4/1997 | Waranis et al. |
| 5,665,772 A | 9/1997 | Cottens et al. |
| 5,780,462 A | 7/1998 | Lee et al. |
| 5,985,325 A | 11/1999 | Nagi |
| 5,989,591 A | 11/1999 | Nagi |
| 6,015,809 A | 1/2000 | Zhu et al. |
| 6,121,319 A | 9/2000 | Somers |
| 2002/0107206 A1 * | 8/2002 | Coolidge et al. .............. 514/21 |

FOREIGN PATENT DOCUMENTS

| | | |
|---|---|---|
| EP | 0 525 960 A1 | 2/1993 |
| WO | WO 96/17845 | 6/1996 |
| WO | WO 97/35575 | 10/1997 |
| WO | WO 98/56358 | 12/1998 |

OTHER PUBLICATIONS

The Merck Manual of Diagnosis and Therapy, 14th Ed., published 1982 by Merck Sharp & Dohme Research Laboratories.*

C.V. Vezina et al., J. Anitbiot., 1975, 721, 28.

H.A. Baker et al., J. Anitbiot., 1978, 539, 31.

FASEB, 1989, 3411, 3.

FASEB, 1989, 5256, 3.

R.Y. Calne et al., Lancet, 1978, 1183.

R. Martel et al., Can. J. Physiol. Pharmacol., 1977, 48, 55.

T. Matsumoto et al., Atuoschlerosis, 1998, 95, 139.

S.E. Roselaar et al., J. Clin. Invest., 1995, 1906, 96.

K.B. Lemstrom et al., Arterioscler, Thomb. Vasc. Biol., 1996, 553, 16(4).

T. Quaschning et al., Kidney Int., 1999, S235, 56(71).

E.E. Emeson et al., Am. J. Pathol., 1993, 1906, 142(6).

* cited by examiner

*Primary Examiner*—Raymond Henley, III
(74) *Attorney, Agent, or Firm*—Howson and Howson; Arnold S. Milowsky

(57) ABSTRACT

This invention provides a method of treating or inhibiting cardiovascular, cerebral vascular, or peripheral vascular disease in a mammal in need thereof, which comprises providing said mammal with an effective amount of a rapamycin.

12 Claims, No Drawings

METHOD OF TREATING CARDIOVASCULAR DISEASE

This application is a continuation-in-part of U.S. patent application Ser. No. 09/880,295, filed Jun. 13, 2001, now abandoned which claims the benefit of U.S. Provisional Application No. 60/212,117, filed Jun. 16, 2000.

BACKGROUND OF THE INVENTION

This invention relates the use of a rapamycin in the treatment and inhibition of cardiovascular disease, cerebral vascular disease, and peripheral vascular disease.

Coronary artery disease, the primary form of cardiovascular disease (CVD), is the major cause of death in the United States today, responsible for over 550,000 deaths per year. Cerebrovascular disease is the third leading cause of death in the United States. The etiology of both coronary artery and cerebrovascular diseases is attributed to atherosclerosis. Through its clinical manifestations, atherosclerosis is the major cause of the more than one million heart attacks and approximately 400,000 strokes that occur each year. In addition to the high morbidity and mortality associated with atherosclerosis, it has been estimated that atherosclerosis has cost the United States' economy over $80 billion each year in lost wages, lost productivity, and medical care costs [Levy, R., Am. Heart J. 110: 1116 (1985)]. A substantial body of evidence has established a relationship between hypercholesterolemia and premature atherosclerosis; the higher the levels of plasma cholesterol, the greater the risk of subsequent heart attack. [Steinberg, D., JAMA 264: 3047 (1991); Lipid Research Clinics Program, JAMA 251: 351 (1984); Rifkind, B., Am. J. Cardiol. 54: 30C (1984)]. However, recent information demonstrates that the atherosclerotic process is far more complicated than a simple correlation with plasma lipid levels, and that there are both systemic and local factors within the vascular wall that play a major role in the progression of this disease [Sulistiyani, Adelman, S. J., Chandrasekaran, A., Jayo, J. and St. Clair, R. W. Arteriosclerosis and Thrombosis 15: 837, (1995)].

Atherosclerosis is a complex disease that is associated with a variety of etiologic factors. Studies have shown that, of the major factors involved, diet-induced hyperlipidemia and genetic defects or abnormalities in lipoprotein metabolism have received the most attention. The local disease process of atherosclerosis is characterized by the accumulation of lipids in the walls of blood vessels. Concomitant with lipid accumulation, there is vascular cell damage resulting in dysfunction of the endothelium, smooth muscle proliferation, and matrix deposition. These changes ultimately result in the formation of what is termed "plaque". As these plaques expand and mature, ruptures in their surface can occur, leading to major thrombotic events. This process, which can occur in essentially all of the blood vessels of the body, results in many of the major disease categories of our time, including coronary artery disease, peripheral vascular disease, myocardial infarction and stroke.

The lipid component of atherosclerotic plaque is of major significance to a variety of vascular diseases. As the plaque develops, there are regions that are rich in cellular material and matrix, underlying a metabolically stable condition. On the luminal surface (contacting the flowing blood) of the plaque, there is a region that further stabilizes the plaque, referred to as the "cap". In these stable regions of the plaque, the cap is relatively thick, and maintains the vessel in a non-threatening elastic state. In contrast to these stable regions, and of up-most importance, there exist other regions of the lesion that are highly enriched in lipid. These regions are the least cellular, with the least amount of connective material for strength and protection from breakage. Cardiac events are often associated with a breakage or rupture of this cap, exposing the flowing blood to the underlying, highly pro-thrombotic material within the plaque, resulting in blockage. Recent studies have found that regions of the plaque most likely to rupture are those with the greatest lipid content. It is typically these lipid rich, soft, pliable regions of the atherosclerotic plaque that give way and rupture (Falk and Fuster et. al), inducing the subsequent thrombotic events that ultimately result in vessel blockage and major vascular events. Therefore, it the lipid-rich regions of the plaque are prominent as contributors to major cardiovascular events such as myocardial infarction and stroke.

In addition to the lipid component, it has recently, been discovered that cells of the immune system also play a major role in all of the processes of atherosclerosis, and thus the process has been described as a chronic inflammatory-fibroproliferative disease of the vascular wall. This is in addition to the lipid deposition typically recognized as atherosclerosis. The attachment of monocytes and T-lymphocytes to the injured endothelium followed by their migration into the intima is one of the first and most crucial steps in lesion development. The co-localization of CD4+ T-cells and macrophages in the lesion, the abundant expression of HLA Class II molecules and the co-stimulatory molecule CD40 and its ligand (CD40L) indicate a contribution of cell-mediated immunity to atherogenesis. A wide variety of studies in animal models suggest that T- and B-cells, and monocytes and macrophages promote lesion progression, and in fact, are in essential for the development of atherosclerotic lesions. Importantly, the local vascular wall immune contribution continues throughout, participating in both plaque expansion as well as rupture. In addition to the local process in the vessel wall, systemic signs of an inflammatory reaction are also associated with lesion development. Thus plasma levels of C-reactive protein and fibrinogen and the white blood cell count are positively correlated to the risk of cardiovascular disease.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

DESCRIPTION OF THE INVENTION

This invention provides a method of treating or inhibiting cardiovascular disease or peripheral vascular disease in a mammal in need thereof, based on our newly discovered and unanticipated effect on vascular wall lipid accumulation, which comprises providing an effective amount of a rapamycin to said mammal. As defined herein, the term "a rapamycin" defines a class of immunosuppressive compounds which contain the basic rapamycin nucleus (shown below). The rapamycins of this invention include compounds which may be chemically or biologically modified as derivatives of the rapamycin nucleus, while still retaining immunosuppressive properties. Accordingly, the term "a rapamycin" includes esters, ethers, oximes, hydrazones, and hydroxylamines of rapamycin, as well as rapamycins in which functional groups on the rapamycin nucleus have been modified, for example through reduction or oxidation. The term "a rapamycin" also includes pharmaceutically acceptable salts of rapamycins, which are capable of forming such salts, either by virtue of containing an acidic or basic moiety.

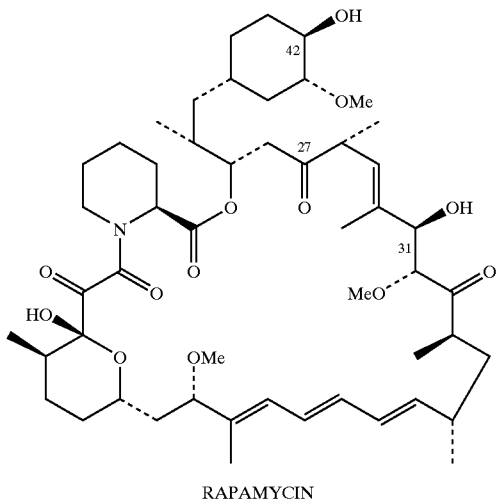

RAPAMYCIN

It is preferred that the esters and ethers of rapamycin are of the hydroxyl groups at the 42- and/or 31-positions of the rapamycin nucleus, esters and ethers of a hydroxyl group at the 27-position (following chemical reduction of the 27-ketone), and that the oximes, hydrazones, and hydroxylamines are of a ketone at the 42-position (following oxidation of the 42-hydroxyl group) and of 27-ketone of the rapamycin nucleus.

Preferred 42- and/or 31-esters and ethers of rapamycin are disclosed in the following patents, which are all hereby incorporated by reference: alkyl esters (U.S. Pat. No. 4,316, 885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118, 678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258, 389); carbonate esters (U.S. Pat. No. 5,260,300); arylcarbonyl and alkoxycarbonyl carbamates (U.S. Pat. No. 5,262, 423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463, 048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers are disclosed in the patents listed above.

Preferred 27-esters and ethers of rapamycin are disclosed in U.S. Pat. No. 5,256,790, which is hereby incorporated by reference. The preparation of these esters and ethers are disclosed in the patents listed above.

Preferred oximes, hydrazones, and hydroxylamines of rapamycin are disclosed in U.S. Pat. Nos. 5,373,014, 5,378, 836, 5,023,264, and 5,563,145, which are hereby incorporated by reference. The preparation of these oximes, hydrazones, and hydroxylamines are disclosed in the above listed patents. The preparation of 42-oxorapamycin is disclosed in 5,023,263, which is hereby incorporated by reference.

Particularly preferred rapamycins include rapamycin [U.S. Pat. No. 3,929,992], rapamycin 42-ester with 3-hydroxy-2-(hydroxymethyl)-2-methylpropionic acid [U.S. Pat. No. 5,362,718], and 42-O-(2-hydroxy)ethyl rapamycin [U.S. Pat. No. 5,665,772].

When applicable, pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when the rapamycin contains a suitable basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when the rapamycin contains a suitable acidic moiety.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

The ability of the rapamycins of this invention to treat or inhibit cardiovascular disease or peripheral vascular disease was confirmed in a standard pharmacological test procedure using ApoE knockout (EKO) mice, which are a well accepted animal model of human atherosclerosis. In this test procedure, rapamycin was used a representative example of a rapamycin of this invention. The procedure used, and results obtained are briefly summarized below.

Male EKO mice, 4–6 weeks of age, were housed in shoe-box cages and were allowed ad lib food and water. The animals were randomized by weight into 5 groups (N=12–15 mice per group) and were fed Purina Rodent Chow for the first week of the study. Also during this period as well as the remaining 12 weeks of the study, the animals were dosed every 2 days with 0, 1, 2, 4 or 8 mg/kg rapamycin s.c. using 2% Tween-80, 1% carboxymethyl cellulose as the vehicle and Control. The animal diet was switched to a casein-based Western Diet for week 2 to week 13 of the study. At the end of the study period, the animals were euthanized, plasma samples obtained, and the hearts perfused first with saline, then with 10% formalin. Total cholesterol and triglycerides were determined using enzymatic methods with commercially-available kits from Boehringer Mannheim and Wako Biochemicals, respectively, and the Boehringer Mannheim Hitachii 911 Analyzer (Boehringer Mannheim Diagnostic Laboratory Systems, Indianapolis, Ind.). Separation and quantification of plasma lipoproteins were performed using FPLC size fractionation. Briefly, 50–100 ml of serum was filtered and injected into two Superose 6 columns (Amersham Pharmacia Biotech, UK, Ltd) connected in series and eluted at a constant flow rate with 1 mM sodium EDTA and 0.15 M NaCl. Areas of each curve representing VLDL, LDL and HDL were integrated using Millennium software (Waters Technologies Corporation), and each lipoprotein fraction was quantified by multiplying the Total Cholesterol value by the relative percent area of each respective peak. The aortas were carefully isolated and remained in the formalin fixative for 48–72 hours before handling. Atherosclerotic lesions were identified by Oil Red O staining, a well accepted procedure for identifying accumulation of neutral lipids such as cholesterols and triglycerides. The vessels were destained, and then imaged using a Nikon SMU800 microscope fitted with a Sony 3CCD video camera system in concert with IMAQ Configuration Utility (National Instrument) as the image capturing software. The lesions were quantified along the aortic arch using a custom threshold utility software package designed by Robert Coll (Coleman Technologies). Automated lesion assessment was performed on the vessels using the threshold function of the program, specifically on the region contained within the aortic arch from the proximal edge of the Right Common Carotid artery to the distal edge of the Left Subclavian artery. Aortic atherosclerosis data were expressed as percent lesion (lipid) involvement strictly within this defined luminal area. Statistical significance between the Control and treated groups was determined using the Dunnett's Test at 1% significance level ($p<0.01$).

The following table summarizes the results obtained in this standard pharmacological test procedure for atherosclerosis.

TABLE 1

The Effect of Rapamycin on Plasma Lipids and Aortic Atherosclerosis in Apo E Deficient mice

| Dosage | Triglycerides (mg/dl) | Total Cholesterol (mg/dl) | VLDL-C (mg/dl) | LDL-C (mg/dl) | HDL-C (mg/dl) | Aortic Atherosclerosis (% lesion involvement as assessed by lpipd staining) |
|---|---|---|---|---|---|---|
| Control | 104 ± 13 | 1186 ± 47 | 807 ± 48 | 371 ± 13 | 7 ± 3 | 39.5 ± 2.6 |
| 1 mg/kg[+] | 132 ± 16 | 1434 ± 35 | 903 ± 34 | 508 ± 18* | 23 ± 6 | 21.6 ± 3.1* |
| 2 mg/kg | 143 ± 20 | 1311 ± 80 | 763 ± 64 | 517 ± 18* | 31 ± 5* | 14.9 ± 3.1* |
| 4 mg/kg | 136 ± 12 | 1281 ± 58 | 749 ± 58 | 494 ± 10* | 38 ± 5* | 16.4 ± 2.8* |
| 8 mg/kg | 134 ± 9 | 1167 ± 75 | 644 ± 58 | 475 ± 21* | 49 ± 3* | 12.03 ± 2.3* |

Data are mean ± S.E.
[+]Dosage of rapamycin.
*Significantly different from Control group ($p < 0.01$).

The results in Table I show that treatment with rapamycin significantly ($p<0.01$) increased levels of circulating plasma HDL-cholesterol and LDL-cholesterol, while not significantly affecting levels of triglycerides, total cholesterol, and VLDL-cholesterol compared with control EKO mice. Table I also shows a marked and dramatic decrease in the level of atherosclerosis (lipid deposition) in the rapamycin treated mice. While animals of the Control group demonstrated a mean lesion involvement in the aortic arch of 39.6%, atherosclerosis in animals treated with rapamycin was only 21.6% involvement at 1 mg/kg and decreased further to 14%, 16%, and 12% at the 2, 4, and 8 mg/kg dosages, respectively. This represents a dramatic three-fold reduction in aortic atherosclerosis in a well accepted model of human atherosclerosis.

The results also show that rapamcyin protects against fat accumulation in the vascular wall, and the development of the classically described, atherosclerotic disease. In studies utilizing a well-accepted in vivo model of atherosclerosis, the apoprotein E deficient mouse, we have found that lipid accumulation in the blood vessels is significantly and dramatically reduced. Animals not treated with rapamycin had approximately 40% of their aorta engorged with lipid. In contrast, those treated with rapamycin at 1, 2, 4, or 8-mg/kg qod for 12 weeks had only 12–16% of the area containing fat. This was found despite the observation that circulating total cholesterol in these animals was approximately 1300–1500 mg/dl. The NCEP guidelines recommend that humans are at significantly increased risk of developing atherosclerosis and cardiovascular disease if their total cholesterol exceeds 180–200 mg/dl. Thus despite the substantial elevation of lipids in circulation in these animals, rapamycin had a substantial effect on reducing atherosclerotic disease.

Based on the results obtained in the standard pharmacological test procedure described above, rapamycins are useful in the treatment or inhibition of cardiovascular disease and peripheral vascular disease. More particularly, the rapamycins of this invention are useful in treating or inhibiting coronary artery disease, cerebrovascular disease, arteriosclerosis, atherosclerosis, nonatheromatous arteriosclerosis, vascular wall damage from cellular events leading toward immune mediated vascular damage, lipid deposition or accumulation in the vascular wall, acute coronary syndrome, or ischemic reperfusion injury. The rapamycins of this invention are also useful inhibiting stroke, transient ischemic attack, or multiinfarct dementia.

In accordance with this invention, contemplated that a rapamycin may be used as the sole active ingredient to provide the cardiovascular, cerebral, or peripheral vascular benefits covered by this invention, or may be administered in combination with other agents which provide beneficial cardiovascular, cerebral, or peripheral vascular effects. Such agents are generally in the classes of compounds known as ACE inhibitors, such as quinapril, perindopril, ramipril, captopril, trandolapril, fosinopril, lisinopril, moexipril, and enalapril; angiotensin II receptor antagonists, such as candesartan, irbesartan, losartan, valsartan, and telmisartan; fibric acid derivatives, such as clofibrate, and gemfibrozil; HMG Co-A reductase inhibitors, such as cerivastatin, fluvastatin, atorvastatin, lovastatin, pravastatin, simvastatin; beta adrenergic blocking agents, such as sotalol, timolol, esmolol, carteolol, propranolol, betaxolol, penbutolol, nadolol, acebutolol, atenolol, metoprolol, and bisoprolol; calcium channel blockers, such as nifedipine, verapamil, nicardipine, diltiazem, nimodipine, amlodipine, felodipine, nisoldipine, and bepridil; antioxidants; anticoagulants such as, warfarin, dalteparin, heparin, enoxaparin, and danaparoid; and agents useful in hormone replacement therapy containing estrogens, such as conjugated estrogens, ethinyl estradiol, 17-beta-estradiol, estradiol, and estropipate.

It is understood that the effective dosage of a rapamycin may vary depending upon the particular compound utilized, the mode of administration, the condition, and severity thereof, of the condition being treated, as well as the various physical factors related to the individual being treated. As used in accordance with invention, satisfactory results may be obtained when the rapamycin is administered in a daily oral dosage of from about 5 $\mu$g to 0.75 mg per kilogram of body weight. The projected daily dosages are expected to vary with route of administration. With respect to treating acute coronary syndrome, it is preferred that treatment is provided for at least days 1–30, after the initial event, although shorter or longer treatment periods may be warranted depending on the specific patient receiving treatment.

When a rapamycin is used as part of a combination regimen, dosages of each of the components of the combination are administered during a desired treatment period. The components of the combination may administered at the same time; either as a unitary dosage form containing both components, or as separate dosage units; the components of the combination can also be administered at different times during during a treatment period, or one may be administered as a pretreatment for the other.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. It is more preferred that poloxamer 188 is used as the surface modifying agent. Oral formulations herein may utilize standard delay or time release formulations to alter the absorption of the active compound(s). Preferred oral formulations of rapamycins are disclosed in U.S. Pat. Nos. 5,559,121; 5,536,729; 5,989,591; and 5,985,325, which are hereby incorporated by reference. Preferred oral formulations for rapamycin 42-ester with 3-hydroxy-2-(hydroxymethyl)-2-methylpropionic acid are disclosed in U.S. Ser. No. 60/411,264, which is hereby incorporated by reference.

In some cases it may be desirable to administer the compounds directly to the airways in the form of an aerosol.

The compounds of this invention may also be administered parenterally or intraperitoneally, or local directly to the vascular wall. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred parenteral formulations for administering a rapamycin are disclosed in U.S. Pat. Nos. 5,530,006; 5,516,770; and 5,616,588, which are hereby incorporated by reference. Preferred injectable formulations for rapamycin 42-ester with 3-hydroxy-2-(hydroxymethyl)-2-methylpropionic acid are disclosed in U.S. S No. 60/399,526, which is hereby incorporated by reference.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

What is claimed is:

1. A method of treating or inhibiting acute coronary syndrome in a mammal in need thereof, which comprises providing said mammal with an effective amount of a rapamycin.

2. The method according to claim 1, wherein the rapamycin is rapamycin.

3. The method according to claim 1, wherein the rapamycin is a ester, ether, oxime, hydrazone, or hydroxylamine of rapamycin.

4. The method according to claim 3, wherein the rapamycin is a 42-ester or 42-ether of rapamycin.

5. The method according to claim 4, wherein the rapamycin is rapamycin 42-ester with 3-hydroxy-2-(hydroxymethyl)-2-methylpropionic acid.

6. The method according to claim 4, where in the rapamycin is 42-O-(2-hydroxy)ethyl rapamycin.

7. A method of treating or inhibiting ischemic reperfusion injury in a mammal in need thereof, which comprises providing said mammal with an effective amount of a rapamycin.

8. The method according to claim 7, wherein the rapamycin is rapamycin.

9. The method according to claim 7, wherein the rapamycin is a ester, ether, oxime, hydrazone, or hydroxylamine of rapamycin.

10. The method according to claim 9, wherein the rapamycin is a 42-ester or 42-ether.

11. The method according claim 10, wherein the rapamycin is rapamycin 42-ester with 3-hydroxy-2-(hydroxymethy)-2-methylpropionic acid.

12. The method according to claim 10, wherein the rapamycin is 42-O-(2-hydroxy)ethyl rapamycin.

* * * * *